United States Patent
Sylvain

(10) Patent No.: US 8,127,001 B1
(45) Date of Patent: Feb. 28, 2012

(54) METHOD AND SYSTEM FOR SELECTING PROVIDERS FOR ROLE BASED SERVICES

(75) Inventor: Dany Sylvain, Gatineau (CA)

(73) Assignee: Rockstar Bidco, LP, New York, NY (US)

( * ) Notice: Subject to any disclaimer, the term of this patent is extended or adjusted under 35 U.S.C. 154(b) by 180 days.

(21) Appl. No.: 12/246,321

(22) Filed: Oct. 6, 2008

(51) Int. Cl.
G06F 15/16 (2006.01)
G06F 15/173 (2006.01)
G06F 15/177 (2006.01)

(52) U.S. Cl. ............ 709/224; 370/392; 370/461; 705/2; 705/3

(58) Field of Classification Search .......... 709/217–228; 705/2, 3; 370/461, 392
See application file for complete search history.

(56) References Cited

U.S. PATENT DOCUMENTS

| | | | | |
|---|---|---|---|---|
| 7,466,810 | B1* | 12/2008 | Quon et al. | 379/201.01 |
| 2007/0061361 | A1* | 3/2007 | Tanaka et al. | 707/104.1 |
| 2007/0100981 | A1* | 5/2007 | Adamczyk et al. | 709/223 |
| 2007/0160077 | A1* | 7/2007 | Altberg et al. | 370/461 |
| 2007/0161386 | A1* | 7/2007 | Faber et al. | 455/508 |
| 2007/0162334 | A1* | 7/2007 | Altberg et al. | 705/14 |
| 2007/0165608 | A1* | 7/2007 | Altberg et al. | 370/352 |
| 2007/0165640 | A1* | 7/2007 | Fitchett et al. | 370/392 |
| 2007/0165641 | A1* | 7/2007 | Fitchett et al. | 370/392 |
| 2007/0165804 | A1* | 7/2007 | Altberg et al. | 379/114.03 |
| 2007/0165821 | A1* | 7/2007 | Altberg et al. | 379/210.02 |
| 2007/0165841 | A1* | 7/2007 | Faber et al. | 379/441 |
| 2007/0167170 | A1* | 7/2007 | Fitchett et al. | 455/456.1 |
| 2007/0287488 | A1* | 12/2007 | Faber et al. | 455/508 |
| 2007/0291683 | A1* | 12/2007 | Bonner et al. | 370/328 |
| 2008/0018436 | A1* | 1/2008 | Traughber et al. | 340/286.07 |
| 2008/0101573 | A1* | 5/2008 | Sylvain | 379/201.01 |
| 2008/0162637 | A1* | 7/2008 | Adamczyk et al. | 709/204 |
| 2008/0194260 | A1* | 8/2008 | Altberg et al. | 455/435.1 |
| 2009/0089088 | A1* | 4/2009 | Schoenberg | 705/2 |
| 2009/0248883 | A1* | 10/2009 | Suryanarayana et al. | 709/229 |
| 2009/0279681 | A1* | 11/2009 | Mckee et al. | 379/201.02 |
| 2009/0279683 | A1* | 11/2009 | Gisby et al. | 379/201.02 |
| 2010/0077082 | A1* | 3/2010 | Hession et al. | 709/227 |
| 2010/0094659 | A1* | 4/2010 | Schoenberg | 705/3 |

\* cited by examiner

*Primary Examiner* — Haresh N Patel
(74) *Attorney, Agent, or Firm* — Withrow & Terranova, PLLC

(57) ABSTRACT

The present invention allows individual providers to be assigned to one or more roles. A role corresponds to a function, service, or action that can be fulfilled by the provider who is assigned to the role. A media session may be initiated by sending a session request from a requester toward a given role instead of being initiated directly to a particular provider. The media session may include a voice or video call, instant messaging session, file transfer session, application sharing session, or the like. The session request is routed to a role server, which may direct the session request to the provider who is assigned to the corresponding role. Once a decision is made to route the session request to a particular provider, provider routing rules may further control how the session requests are routed to the provider terminals of the particular provider.

30 Claims, 12 Drawing Sheets

| ACTIVE ROLE ASSIGNMENTS | | PROVIDER SELECTION RULES | |
|---|---|---|---|
| ROLE | ASSIGNED PROVIDERS | NORMAL | URGENT |
| RADIOLOGIST-ON-DUTY | DR. SMITH<br>DR. TAYLOR<br>BACK-UP-RADIOLOGIST-ON-DUTY | • ROUND ROBIN<br>• EXCLUDE BACK-UP | • ALL<br>• INCLUDE BACK-UP |
| CARDIOLOGIST-ON-DUTY | DR. ADAMS<br>DR. RUIZ | • FIRST ON LIST | • ALL |
| BACK-UP-RADIOLOGIST-ON-DUTY | DR. JONES | • ASSIGNED PROVIDER | • ASSIGNED PROVIDER |
| GENERALIST-ON-DUTY | DR. EASY<br>DR. READY | • FIRST AVAILABLE | • ALL |
| CODE-BLUE-TEAM | CARDIOLOGIST-ON-DUTY<br>GENERALIST-ON-DUTY | • N/A | • ALL |

*FIG. 5*

| SCHEDULED ROLE ASSIGNMENTS | | |
|---|---|---|
| RADIOLOGIST-ON-DUTY | MONDAY | |
| 00:00-8:00 | DR. JONES | |
| 8:00-16:00 | DR. SMITH | |
| 16:00-00:00 | DR. TAYLOR | |

*FIG. 6*

METHOD AND SYSTEM FOR SELECTING PROVIDERS FOR ROLE BASED SERVICES

FIELD OF THE INVENTION

The present invention relates to providing services to requesters and in particular to dynamically selecting providers to provide services to requesters.

BACKGROUND OF THE INVENTION

In many environments, there is a need for callers to be connected with human agents that have a particular expertise in a given area. In many cases, different agents will have expertise in different areas, and connecting each caller to an agent that has expertise in a desired area faces various challenges. For instance, there are generally numerous agents that have expertise in given area, and these agents rotate in and out of availability based on their work schedule, breaks, and servicing other callers. Being able to identify an agent that has expertise in a given area, determine whether the agent is available, and connect the caller to the agent is typically provided manually or through an automated call center. Manual processes that rely on operators keeping track of an agent's expertise and availability, which may be in a constant state of flux, is at best inefficient and generally impracticable. Using a hospital environment as an example, hospital operators have a very difficult time keeping track of which nurses and doctors are at work, let alone keeping track of the particular specialties of the nurses and doctors and whether they are available at any given time to respond to a caller's request.

Call centers are relatively structured systems configured to route calls from various callers to terminals of agents who are capable of servicing the needs of the callers. Each agent must login to an agent terminal to make herself available for handling calls. Once logged in via their terminals, the agents are associated with a certain area of expertise, and it is assumed that the agent logged into the terminal has expertise in the certain area. As such, agents are either in or out of an available pool of agents for handling calls based on whether they are logged into their agent terminal. Callers generally initiate calls to the call center in general, and upon establishing a communication session with the call center, interact with an automated agent or a triage agent to have the communication session transferred to a particular agent terminal.

In addition to being cost prohibitive in many environments, call centers are often restrictive in the sense that the agents must be logged into a particular terminal in the system in order to be considered available for handling calls. Thus, the ability for an agent to dynamically move from one type of terminal to another and still be available to handle calls is limited. Further, it is difficult to make an agent, who is capable of providing different types of services, available to handle different services at the same time. For example, an entity may have a call center configured to direct a technical support request to a first group of terminals and sales support requests to a second group of terminals. A given agent may be able to handle sales support requests as well as technical support requests, but is logged into an agent terminal that is in the first group of terminals that are allocated to technical support requests. As such, the agent may not be engaged in a technical support request while all of the other sales support agents are overloaded with requests.

As such, there is a need for a better technique to connect those who need services to agents who are capable of providing those services through various types of communication sessions, including calls or text communications. There is also a need to provide more flexibility in keeping track of the availability of agents, allow agents that have different capabilities to be able to handle requests corresponding to those capabilities, and provide agents more flexibility in selecting a terminal to use when responding to requests.

SUMMARY OF THE INVENTION

The present invention allows individual providers to be assigned to one or more roles. A role corresponds to a function, service, or action that can be fulfilled by the provider who is assigned to the role. A media session may be initiated by sending a session request from a requester toward a given role instead of being initiated directly to a particular provider. The media session may include a voice or video call, instant messaging session, file transfer session, application sharing session, or the like. The session request is routed to a role server, which may direct the session request to the provider who is assigned to the corresponding role. If multiple providers are assigned to a given role, provider selection rules may be used to select the provider or providers to whom the session request should be routed. The session request may be routed to one or more providers who are assigned to the role. If the session request is routed to multiple providers, the session request may be routed to the multiple providers sequentially or simultaneously. Once a decision is made to route the session request to a particular provider, provider routing rules may further control how the session requests are routed to the provider terminals of the particular provider.

Those skilled in the art will appreciate the scope of the present invention and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the invention, and together with the description serve to explain the principles of the invention.

FIG. 5 is a table illustrating active role assignments according to one embodiment of the present invention.

FIG. 6 is a table illustrating scheduled role assignments according to one embodiment of the present invention.

DETAILED DESCRIPTION OF THE PREFERRED EMBODIMENTS

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

For the present invention, a role corresponds to a function, service, or action that can be fulfilled by a provider. In a given environment, different types of roles may be defined and may correspond to different functions, services, or actions. One or more providers may be assigned to the different types of roles. Further, a single provider may be assigned to different roles at the same or different times. Those skilled in the art will recognize the flexibility in assigning providers with various capabilities to appropriate roles.

A media session may be initiated by sending a session request from a requester toward a given role instead of being initiated directly to a particular provider. The media session may include a voice or video call, instant messaging session, file transfer session, application sharing session, or the like. The session request is routed to a role server, which may direct the session request to the provider who is assigned to the corresponding role. If multiple providers are assigned to a given role, provider selection rules may be used to select the provider or providers to whom the session request should be routed. The session request may be routed to one or more providers who are assigned to the role. If the session request is routed to multiple providers, the session request may be routed to the multiple providers sequentially or simultaneously. Once a decision is made to route the session request to a particular provider is made, provider routing rules may further control how the session requests are routed to the provider terminals of the particular provider. Prior to delving into the details of the present invention, an overview of an exemplary communication environment in which the present invention may be employed is described.

Figure 1:
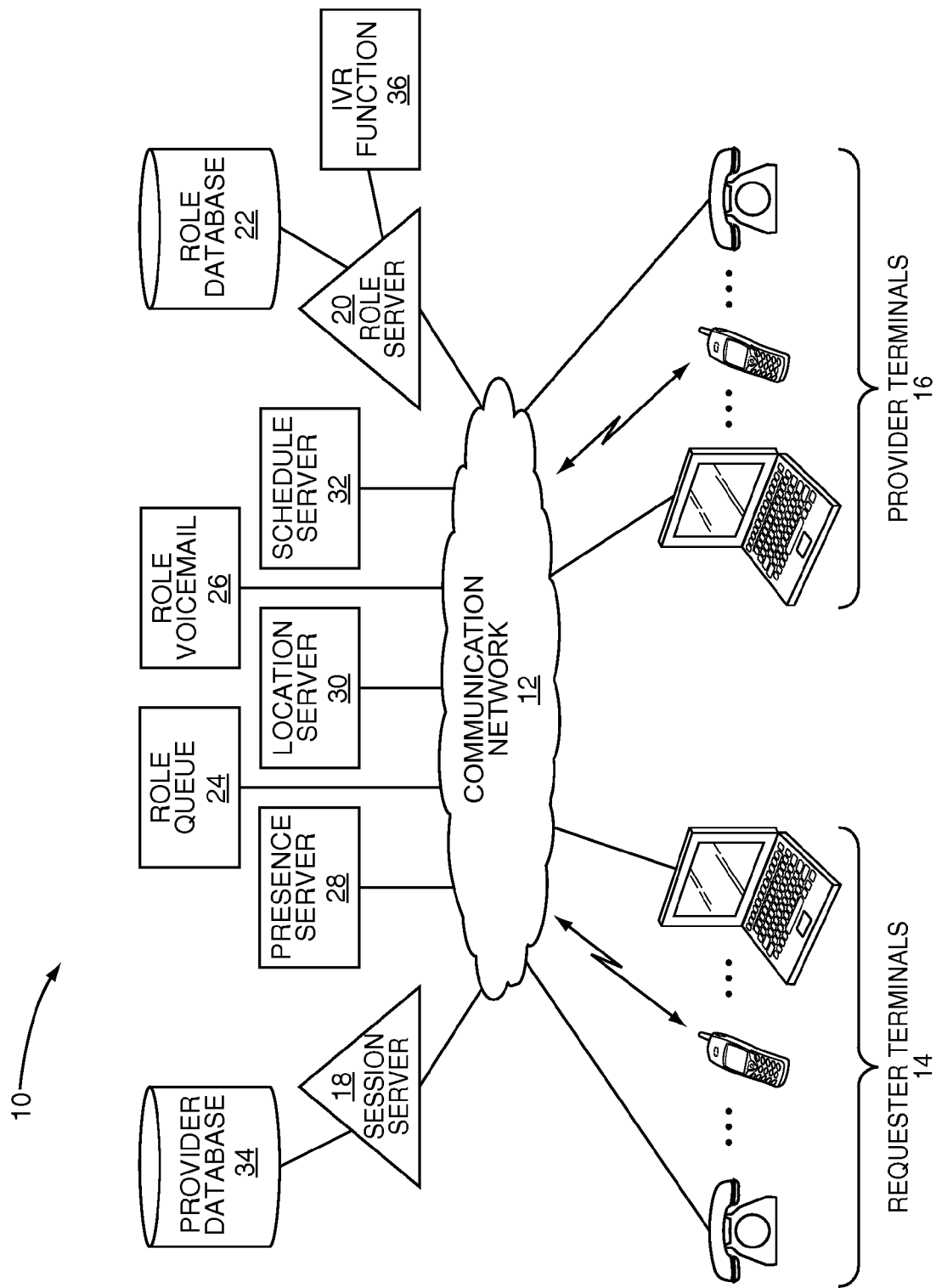
FIG. 1 is a block representation of a communication environment according to one embodiment of the present invention.

With reference to FIG. 1, a communication environment 10 is illustrated to include a communication network 12, which may be formed from any number of packet-based or circuit-switched communication networks, such as the public switched telephone network (PSTN), cellular networks, wireless local area networks, the Internet, and the like. In general, individuals who require the functions, services, or actions of a provider are referred to as requesters. The requesters are associated with one or more requester terminals 14, which may take the form of any type of wired or wireless communication terminal, such as a telephone, personal computer, personal digital assistant, or the like.

Various functions, services, or actions that may need provided to requesters are categorized into roles. Providers that are capable of providing these various functions, services, or actions are assigned to the various roles. The providers are associated with one or more provider terminals 16, which like the requester terminals 14, may take the form of any type of wired or wireless communication terminal, such as a telephone, personal computer, personal digital assistant, or the like. Media sessions are established between requesters of particular roles and providers who are responsive to the roles via the corresponding requester terminals 14 and provider terminals 16. As such, the functions, services, or actions of the various providers may be provided through the media sessions to fulfill needs of the requesters. The media sessions may include any one or combination of voice or video calls, instant messaging sessions, file transfer sessions, application sharing sessions, or the like.

In general, when a requester has a need that can be fulfilled by a particular role, a media session may be initiated by the requester to a particular role, instead of a particular provider. The media session is initiated by sending a session request intended for the role from a requester terminal 14 of the requester. The session request is processed by a session server 18, such as a call server, and routed to a role server 20, which may act as a proxy for the requested role. The role server 20 will process the session request or information associated with the session request to identify the requested role and select a provider who has been assigned to the role. The role server 20 will then route the session request toward the selected provider. The session request may be routed directly to a provider terminal 16 that is associated with the selected provider. Alternatively, if the provider is associated with multiple provider terminals 16, the session request may be routed to the same or different session server 18 described above. The session server 18 will select one or more of the provider terminals 16, which are associated with the selected provider, and route the session request to the selected one or more provider terminals 16 in a desired fashion. Upon acceptance of the session request at a provider terminal 16, a media session is established between the requester terminal 14 and the provider terminal 16. Through the media session, the provider can fulfill the needs of the requester.

Multiple providers may be assigned to a particular role at any given time. As such, the role server 20 has the option of routing the session request for the role to one or more of the providers who are assigned to the role. Provider selection rules may be used to select the provider or providers to whom the session request should be routed and control how the session requests are routed. The role assignment information, which identifies the providers who are assigned to the different roles, and the provider selection rules may reside in a role database 22, which is accessible by the role server 20. Based on the provider selection rules, the role server 20 may select a provider who is assigned to the role and route the session request to the selected provider.

Alternatively, the role server 20 may also select multiple providers who are assigned to the role and route the session request to each of the selected providers at the same time or in sequence. When the role server 20 simultaneously routes the session request to multiple providers, the first provider to accept the session request may be connected with the requester through an appropriate media session. The session request to the remaining providers may be cancelled. For sequential routing, the role server 20 may sequentially route the session request to those providers who are assigned to the role until one of the providers accepts the session request. For example, the role server 20 may select a first provider and route the session request to the first provider. After the first provider fails to respond or rejects the session request, the role server 20 may select a second provider and route the session request to the second provider, and so on and so forth, until a provider responds. The provider selection rules may also control the sequence, or order, in which session requests should be sent to the multiple providers.

Selection of a provider or group of providers for responding to a session request may be based on various criteria embodied by the provider selection rules. For example, a provider may be selected based on a relative priority assigned to the multiple providers who are assigned to the role. A provider may also be selected from the group of available providers based on their position in a list, when they were last selected to respond to a requester, their skill level or capabilities, their availability, and the like. When all providers are considered equal for a role, a random selection or round robin approach may preferably be employed where providers are sequentially selected for consecutive requests, assuming they are available.

If all of the assigned providers are busy assisting other requesters, a new session request may be placed in a role queue 24. As providers become available, the session requests in the role queue 24 are processed and routed to one or more providers. Session requests may also be directed to a role voicemail 26 when there are no providers available to handle the session requests. A session is established with the role voicemail 26 to allow the requester to leave a message for the role or a particular provider. Preferably, voicemail boxes are assigned to each provider or role in general, such that providers may access the appropriate voicemail boxes.

The provider selection rules may take various factors into consideration when selecting one or more providers in response to receiving a session request for a particular role. For example, the provider selection rules may simply systematically go through a list of available providers, wherein each new session request for a given role is directed to the next provider on the list of providers who are assigned to the given role. If the providers for a role are pooled, the provider selection rules may ensure the session requests or overall response efforts are evenly distributed. The provider who has gone the longest without responding to a session request may be selected to respond to the next session request.

The provider routing rules may also take into consideration the type of media session that is required for the session request. For example, different rules may be applied, and thus different providers may be selected, for voice, video, instant messaging, or like media sessions. The providers assigned to a given role may be prioritized with respect to one another. The provider selection rules may be configured to select an available provider with the highest priority.

Notably, any given provider may be associated with the multiple provider terminals 16. As such, a session request that needs to be routed to a given provider may be routed to one, some, or all of the provider terminals 16 of the provider. When the session request is routed to multiple ones of the provider terminals 16 of the provider, the session request may be routed to the provider terminals 16 at the same time or in sequence. Provider routing rules are provided to control the selection of provider terminals 16 for a given provider and the nature in which the session request is routed to the selected provider terminals 16, once a decision is made to route the session request to the given provider. The nature of routing may bear on whether the session requests are routed to a single provider terminal 16 or routed to multiple provider terminals 16 at the same time or in sequence.

The role server 20 may use the provider routing rules to further select the provider terminal or terminals 16 to use when routing a session request to a given provider, and if appropriate, the nature in which the session request is routed. Upon selecting the provider terminals 16 and the nature of routing, the session request is routed to the selected provider terminals 16 accordingly. The provider routing rules may be contained in the role database 22 along with the assignment information and provider selection rules.

Alternatively, the session server 18 may provide this function. For example, the role server 20 may select a provider to which to route the session request and route the session request toward the provider. The session request will be processed by a session server 18. The session server 18 will access the provider routing rules and select the provider terminal or terminals 16 to use when routing a session request to a given provider, and if appropriate, the nature in which the session request is routed. Upon selecting the provider terminals 16 and the nature of routing, the session request is routed by the session server 18 to the selected provider terminals 16 accordingly. In this embodiment, the provider routing rules are located in a provider database 34, which is accessible by the session server 18. Those skilled in the art will recognize that the various rules may be stored in virtually any location and in a separate or integrated fashion.

The role server 20 and the session server 18 may have access to various information sources, such as a presence server 28, a location server 30, and a schedule server 32. The presence server 28 may be configured to provide presence information that pertains to the relative availability of a provider to engage in communications in general or particular types of communications. The presence information may be derived from other information sources that keep track of when the provider is engaged in communications on one or more associated provider terminals 16 or the provider's location, schedule, activities, or the like. The location server 30 specifically keeps track of the provider's actual or relative location while the schedule server 32 keeps track of the provider's schedule, which may be maintained in a calendar application or the like.

Notably, presence, location, schedule, or other like information of or about the provider may be used at various stages of different embodiments of the present invention. For example, such information may be used to dynamically control assignment of the provider to various roles (assignment rules); select a provider who is assigned to a role to respond to a session request (provider selection rules); or route a session request to one or more provider terminals of a provider after the provider has been selected for the session request (provider routing rules). As such, the role server 20, the session server 18, or both may access the same or different information from the presence server 28, the location server 30, the schedule server 32, or other source at the various assignment, selection, and routing stages.

Also illustrated in FIG. 1 is an interactive voice response (IVR) function (or system) 36. The IVR function 36 may be provided by a separate service node or integrated as part of the role server 20 or session server 18. The IVR function 36 effectively provides a voice or dual tone mulifrequency (DTMF) interface for a requester or provider to the role server 20 or other entity in the communication environment 10. The IVR function 36 is capable of receiving information from the role server 20, or other entities, and providing a voice or other audible message over an appropriate session to a corresponding requester or provider. In response, the IVR function 36 is capable of recognizing voice or DTMF instructions provided by the requester or provider and provide corresponding information to the role server 20. Thus, the IVR function 36 represents any type of interactive DTMF or voice interface for a digital system.

Figure 2:
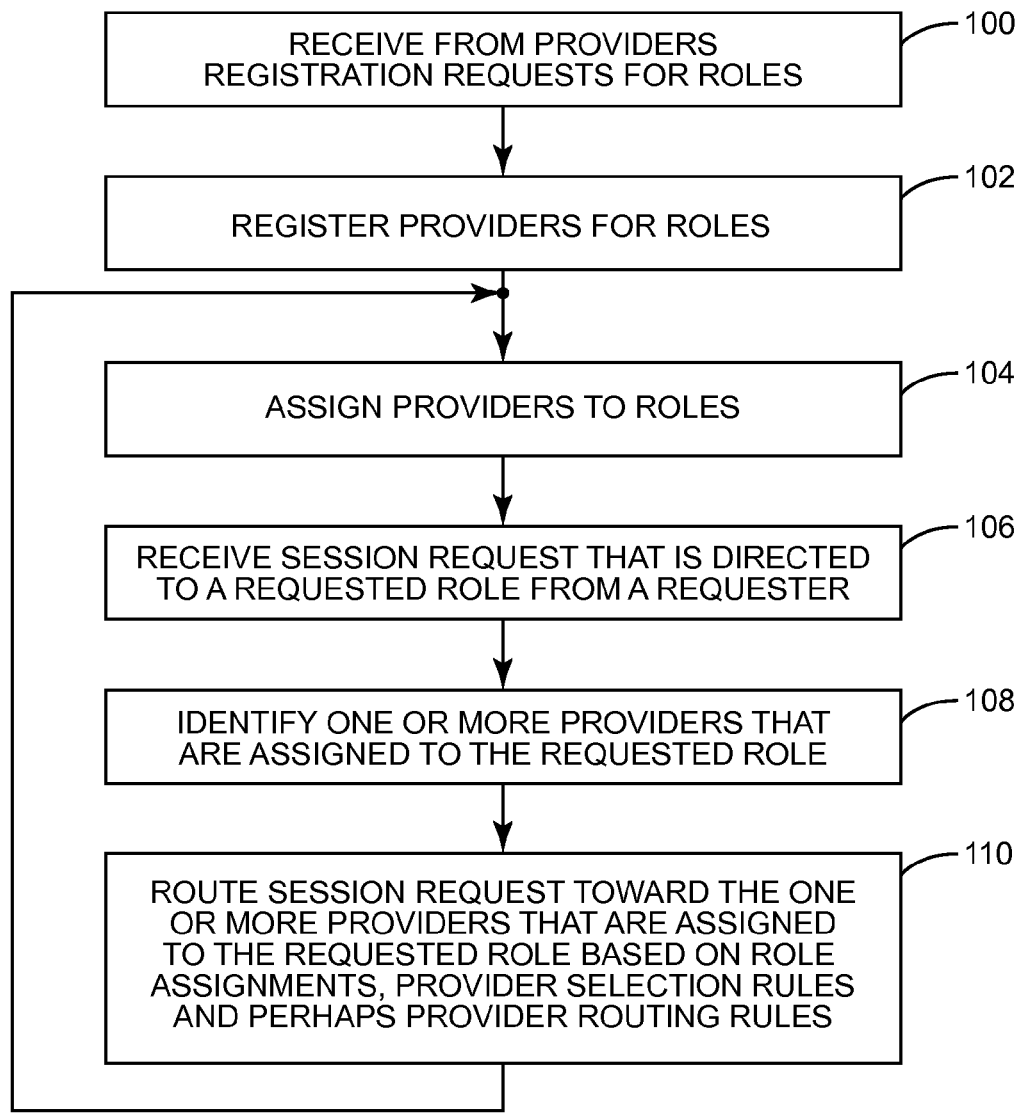
FIG. 2 is a flow diagram illustrating operation of one embodiment of the present invention.

With reference to FIG. 2, a flow diagram is provided to illustrate operation of one embodiment of the present invention. Initially, assume the various providers must register for roles. Any given provider may register for one or more roles, and multiple providers may register for any given role. Notably, the flow diagram of FIG. 2 is provided with reference to the operation of the role server 20. Initially, the role server 20 will receive from the various providers registration requests for any number of roles (step 100). The nature of registration may take various forms. For example, any provider may register for any role in certain embodiments. In other embodiments, only authorized providers, which have the proper credentials, characteristics, capabilities, or the like may register for certain roles. Accordingly, different roles may have different requirements, and only providers that can fulfill those requirements are allowed to register for those roles. Further, providers may require certain authorization, in addition to other criteria, to register for one or more roles. The registration process may require the providers to prove their credentials as well as provide authorization information, which may include providing appropriate user names, user identification, passwords, and the like. Accordingly, the role server 20 will register the various providers for the requested roles (step 102) and assign those providers to the appropriate roles (step 104). Notably, the registration and assignment process may take place on an ongoing basis wherein different providers are systematically registering for roles while other providers are de-registering from roles. As such, the providers that are assigned to the various roles may change in any static or dynamic fashion, depending on the needs and desires of the entity in charge of providing the services.

Once the providers have been assigned to the necessary roles, the providers are capable of fulfilling requests from the various requesters. In this embodiment, requests are generally fulfilled in response to a requester initiating a session toward a specific role. The session is initiated with a session request message, such as a session initiation message. A session initiation message may include a session initiation protocol (SIP) invite or like packet-based session initiator. For circuit-switched embodiments, calls may be initiated toward a directory number associated with the role. Any type of voice, video, text messaging, or other application-based session may be initiated toward a role. The result of initiating the sessions is a session request of some form that is directly or indirectly routed to the role server 20. These session requests may be initially directed to the session server 18, which will forward the session request toward the role server 20 or generated by the session server 18 in response to a requester initiating the session. For the purposes of description, assume the sessions are initiated from a requester terminal 14, which is associated with the requester.

Accordingly, the role server 20 will receive a session request that is directed to a requested role, directly or indirectly, from a requester (step 106). The role server 20 will analyze the session request and identify one or more providers that are assigned to the requested role (step 108). The role server 20 will then route the session request toward the one or more providers that are assigned to the requested role (step 110). In particular, the session request, which may be of the same or different format of that received by the role server 20, is routed to one or more of the provider terminals 16, which are associated with the identified providers. The identification and routing of the session request to the one or more providers is based on the role assignments and any provider selection rules. Again, the provider selection rules may be used to select the provider or providers to whom the session request should be routed in light of the role assignments. The role assignments identify those providers who are assigned to a given role.

In another embodiment of the present invention, the various providers may be associated with multiple provider terminals 16. When a selected provider is associated with multiple provider terminals 16, provider routing rules may be used to determine if, when, or how the session request should be routed to one or more of the available provider terminals 16. Execution of the provider routing rules may be provided by the role server 20 or another entity, such as the session server 18. In the latter case, a session request may be routed to a selected provider. The session request will be received by an appropriate session server 18, which will use the provider routing rules to determine if, when, and how to route the session request to one or more of the provider terminals 16, which are associated with the particular provider. Those skilled in the art will recognize that the functionality provided by the present invention may be integrated or distributed in virtually any manner, without straying from the concepts of the present invention.

Figure 3:
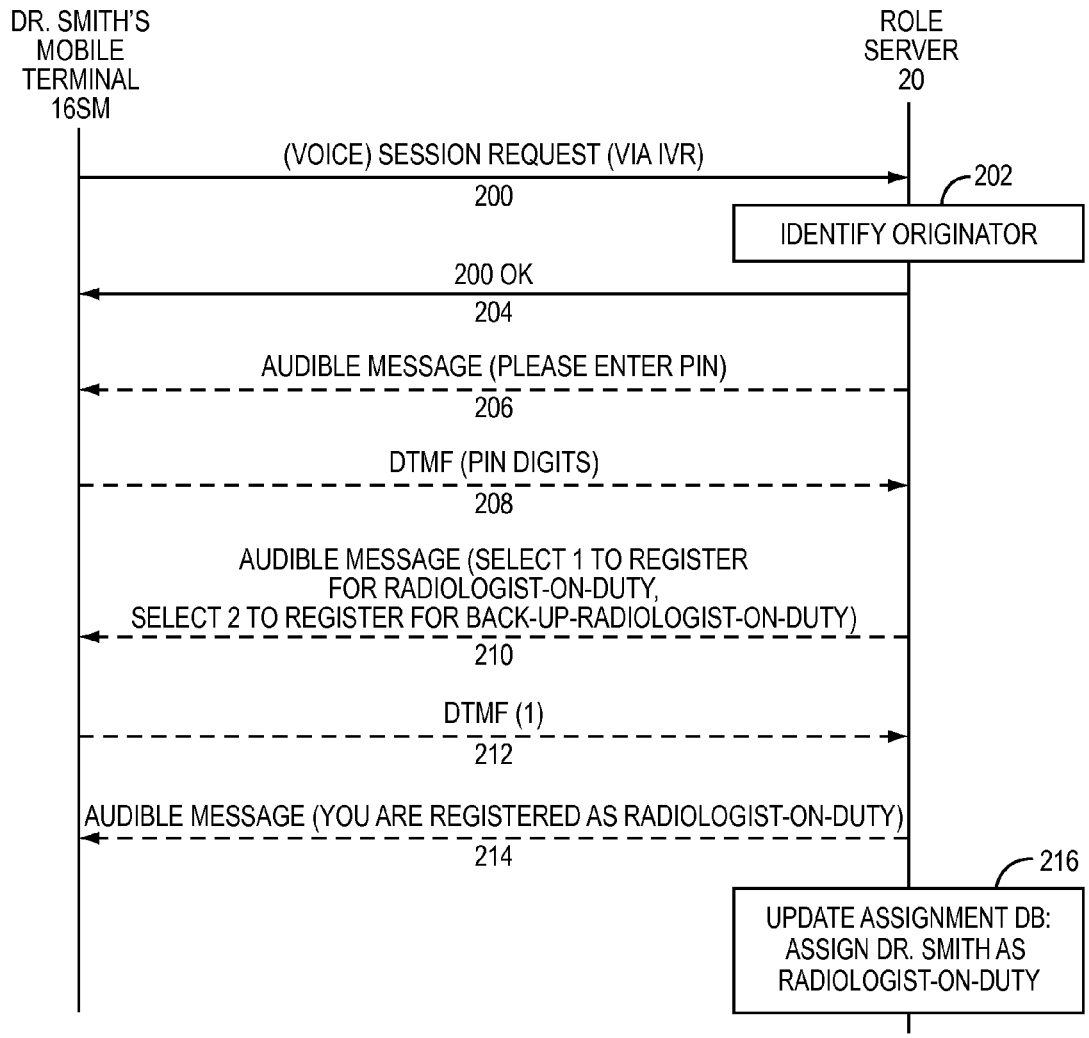
FIG. 3 is a communication flow illustrating a registration process according to one embodiment of the present invention.

With reference to FIG. 3, a communication flow diagram is provided to illustrate registration of a provider to a particular role. In this example, assume the services being provided are medical services and that the providers are doctors who are assigned to various medical roles. In this particular example, Dr. Smith is going to register for a "radiologist-on-duty" role with the role server 20. Dr. Smith is going to register with the role server 20 using her mobile terminal, which is a provider terminal 16, which is referenced as Dr. Smith's mobile terminal 16SM. Notably, the letter "S" corresponds to the first letter of Dr. Smith's surname, while the letter "M" corresponds to the particular provider terminal 16 being a mobile terminal.

With continued reference to FIG. 3, Dr. Smith will initially initiate a voice session through a circuit-switched or packet-based call toward the role server 20. The voice session request is routed to the role server 20 such that the IVR function 36 is invoked for the voice session (step 200). The role server 20 will identify the originator, which is the provider Dr. Smith in this example (step 202). Assuming the session request is a SIP invite, the role server 20 may send a 200 OK message in response to receiving the invite to allow a voice session to be established between Dr. Smith's mobile terminal 16SM and the IVR function 36 of the role server 20 (step 204). A corresponding data session is established between the IVR function 36 and the registration function provided by the role server 20.

Once the voice session is established, the role server 20 will instruct the IVR function 36 to have the provider enter their personal identification number (PIN). As such, the IVR function 36 will deliver an audible message "please enter PIN" to Dr. Smith via the voice session (step 206). Dr. Smith may respond by entering her PIN by pressing the appropriate keys on the keypad of the mobile terminal 16SM. The corresponding DTMF signals for the PIN digits are provided to the IVR function 36, which passes the PIN for Dr. Smith to the role server 20 (step 208). The role server 20 may compare the PIN provided by Dr. Smith with that previously stored in association with Dr. Smith in a corresponding profile to effectively authenticate Dr. Smith and allow her to register for roles in general or particular roles, depending on the configuration of the system.

In this example, assume that the role server 20 authenticates Dr. Smith and recognizes that Dr. Smith is a radiologist and is authorized to register for either a "radiologist-on-duty" role or a "back-up-radiologist-on-duty" role. As such, the role server 20 will instruct the IVR function 36 to send Dr. Smith an audible message to "select 1 to register for 'radiologist-on-duty,' select 2 to register for 'back-up-radiologist-on-duty'..." (step 210). The ellipses merely indicate that further roles may be made available to Dr. Smith. Dr. Smith may respond by pressing the "1" key on her mobile terminal 16SM to register for "radiologist-on-duty." Accordingly, the DTMF signal for "1" is passed to the IVR function 36, which will instruct the role server 20 that Dr. Smith has responded by pressing "1" (step 212). The role server 20 may confirm registration by sending an audible message "you are registered as 'radiologist-on-duty'" to Dr. Smith (step 214). The role server 20 will effectively assign Dr. Smith to the "radiologist-on-duty" role by updating the assignment information in an assignment database to indicate that Dr. Smith is assigned as the "radiologist-on-duty" (step 216). Notably, Dr.

Smith may register for multiple roles, which may be fulfilled concurrently or sequentially. Further, any number of medical professionals may register for one or more roles.

Figure 4:
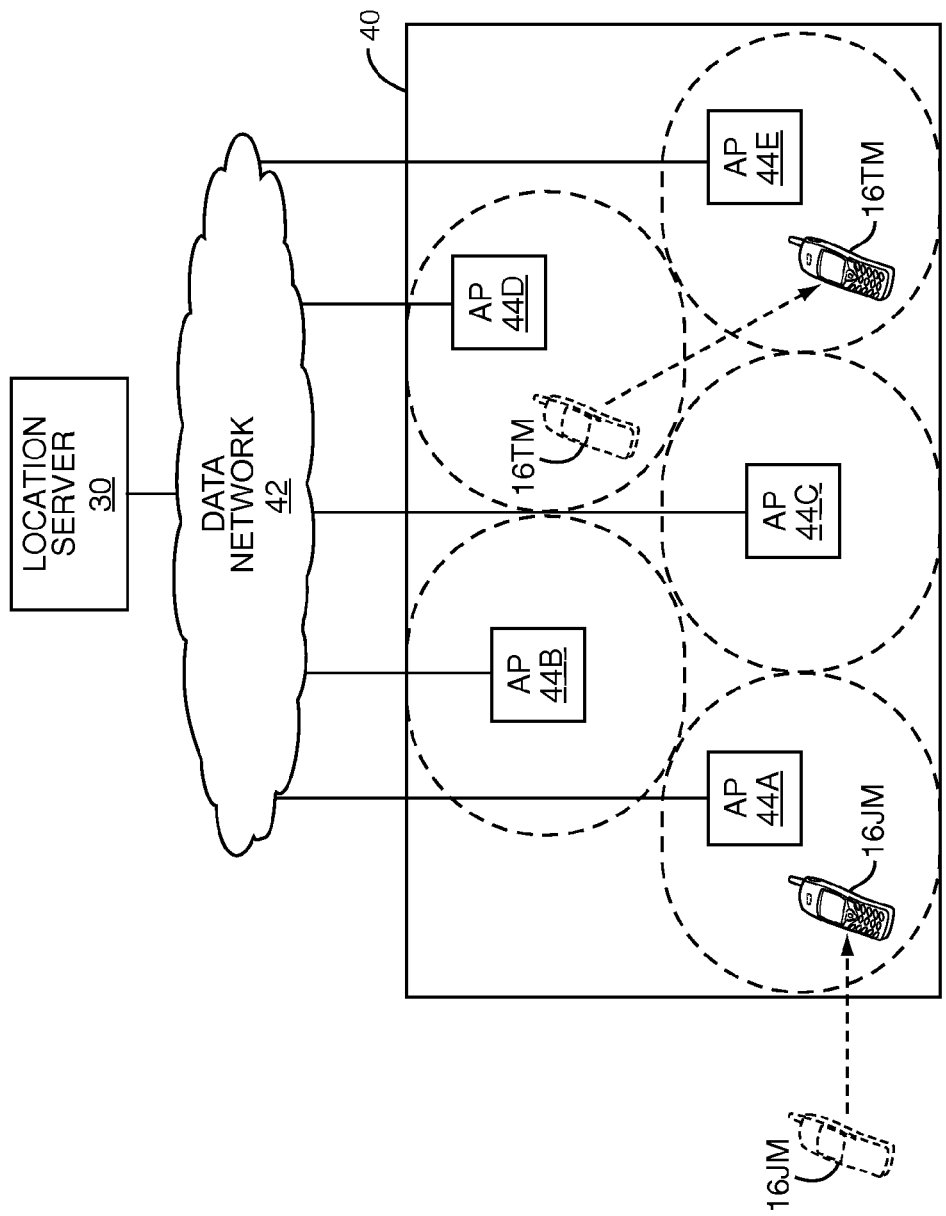
FIG. 4 illustrates a hospital environment wherein assignment of a provider to a particular role is based on the provider's location according to one embodiment of the present invention.

With reference to FIG. 4, another embodiment of the present invention is illustrated. In particular, a hospital environment 40 is served by a data network 42. The data network 42 is coupled to a series of access points (AP) 44A through 44E, which are distributed throughout the hospital environment 40. The access points 44A through 44E provide wireless communications for provider terminals 16, which are within communication range of one or more of the access points 44A through 44E. As illustrated, the mobile terminals of Dr. Jones and Dr. Taylor are illustrated and referenced as 16JM and 16TM, respectively. The dashed arrows represent movement of the corresponding mobile terminals 16JM and 16TM, presumably in association with movement of Dr. Jones and Dr. Taylor, respectively. In particular, the mobile terminal 16JM of Dr. Jones in presumed to have moved from outside of the hospital environment 40 to a zone which is inside the hospital environment 40 and provided by access point 44A. Similarly, the mobile terminal 16TM of Dr. Taylor has moved from a zone associated with access point 44D to a zone associated with access point 44E. Any time a mobile terminal 16JM, 16TM is within communication range of an access point 44A through 44E, appropriate information is recorded by the location server 30 and will be made available to the role server 20, as necessary, to control assignment of Dr. Jones and Dr. Taylor to various roles, according to one embodiment of the present invention. As such, the location server 30 may play a role in the role server 20 dynamically assigning various doctors to different roles based on their location. Similar assignment mechanisms may be established for virtually any type of criteria, including presence information, scheduling information, and the like.

In the present example, assume that rules that control the dynamic assignment of doctors to roles include the following. If Dr. Jones in within the hospital environment 40, assign Dr. Jones to the "back-up-radiologist-on-duty" role. If Dr. Taylor is in the hospital environment 40 and not in a zone defined by access point 44E, assign Dr. Taylor to the "radiologist-on-duty" role. If Dr. Taylor is in the zone defined by the access point 44E, remove Dr. Taylor from the "radiologist-on-duty" role. As such, if the zone associated with the access point 44E corresponds to a surgery room, an assumption can be made that Dr. Taylor is not available to fulfill the "radiologist-on-duty" role because he is in surgery. Otherwise, Dr. Taylor is making his rounds and is available for the "radiologist-on-duty" role. Dr. Jones, on the other hand, may roam throughout the hospital environment 40 and remain assigned to the "back-up-radiologist-on-duty" role until he leaves the hospital environment 40. Those skilled in the art will recognize various ways in which the location server 30 may use information retrieved from the access points 44A through 44E to determine an approximate location of the corresponding provider terminal 16 and make such information available to the role server 20 to dynamically assign the providers to one or more roles based on various assignment criteria.

With reference to FIG. 5, a table is provided to illustrate exemplary role assignments in a medical environment. In this example, the table includes active role assignments for multiple roles. The table identifies a number of roles and providers who are assigned to those respective roles. Also included in the table are provider selection rules. The provider selection rules are broken into two categories, normal and urgent, and define how providers are selected to respond to requests for a role depending on whether the request is normal or urgent.

In particular, five roles are defined. These roles include "radiologist-on-duty," "cardiologist-on-duty," "back-up-radiologist-on-duty," "generalist-on-duty," and "code-blue-team." Notably, Dr. Smith, Dr. Taylor, and a "back-up-radiologist-on-duty" are assigned to the "radiologist-on-duty" role. The provider selection rules are as follows for the "radiologist-on-duty" role. If the request is normal, a round robin approach is taken for Dr. Smith and Dr. Taylor. The "back-up-radiologist-on-duty" is not selected. As such, as requests come in they are alternately provided to Dr. Smith and Dr. Taylor, assuming they are available. If the request is urgent, the provider selection rules will select Dr. Smith, Dr. Taylor, and the "back-up-radiologist-on-duty" and attempt to route the session request either sequentially or simultaneously, depending on the configuration of the system, to these three entities.

Dr. Adams and Dr. Ruiz are assigned to the "cardiologist-on-duty" role. The provider selection rules indicate that normal session requests are always sent to the first doctor on the list, who in this example is Dr. Adams. For urgent session requests, Dr. Adams and Dr. Ruiz are selected and thus, urgent session requests are sent to Dr. Adams and Dr. Ruiz either simultaneously or sequentially. Dr. Jones is assigned to the "back-up-radiologist-on-duty" role. Since Dr. Jones is the only provider assigned to the "back-up-radiologist-on-duty" role, the provider selection rules are minimal and indicate that Dr. Jones will be invoked when the "back-up-radiologist-on-duty" role is selected to route an incoming session request, whether the session request is of normal or urgent priority.

Dr. Easy and Dr. Ready are assigned to the "generalist-on-duty" role. The corresponding provider selection rules dictate that normal session requests are sent to the first available doctor, while urgent session requests are sent to both Dr. Easy and Dr. Ready. For the "code-blue-team" role, the assigned providers are the doctors who are assigned to the "cardiologist-on-duty" role as well as the "generalist-on-duty" role. It is assumed that only urgent session requests are associated with the "code-blue-team" role, and as such, all doctors assigned to the "cardiologist-on-duty" and "generalist-on-duty" will be sent the session request. As such, for session requests directed to the "code-blue-team," Dr. Adams, Dr. Ruiz, Dr. Easy, and Dr. Ready are sent the session request.

When indicating that a session request is sent to a particular provider, it is assumed that the session request is sent to at least one provider terminal 16, which is associated with that particular provider. As indicated above, provider routing rules may be employed at the role server 20, the session server 18, or other entity to control how session requests are routed to more than one provider terminal 16, which is associated with a given provider.

With reference to FIG. 6, another role assignment table is provided according to a second example. In this example, scheduled role assignments are provided for the "radiologist-on-duty" role for a Monday. As illustrated, between 00:00 and 8:00 hours, Dr. Jones is assigned to the "radiologist-on-duty" role. Between 8:00 and 16:00 hours, Dr. Smith is assigned to the "radiologist-on-duty" role, and between 16:00 and 00:00 hours, Dr. Taylor is assigned to the "radiologist-on-duty" role. This example is merely provided to illustrate that there are limitless ways in which to configure role assignments and assign providers to roles. The nature in which providers are assigned is highly configurable and will be based on the needs of the entity providing the services.

Notably, providers may be assigned to a role in various ways. For example, role assignment may be manual or automatic, and if it is automatic, the assignment may be fixed or conditional. As illustrated above, relatively fixed assignments may have a particular provider always assigned to a role or assigned to a role based on a schedule. Conditional assignments may require certain conditions to be fulfilled prior to a provider being assigned to a role. For example, role assignments may be based on presence information, location information, or scheduling information, which is provided by one or more of the presence, location, and schedule servers 28, 30, and 32, or a given provider. For example, if a provider's calendar indicates that the provider is available, and not on vacation or in a meeting, the provider may be assigned to a particular role. If certain location or presence information for the provider indicates that the provider is available for receiving communications, the provider may be assigned to a particular role. Otherwise, if the provider is already engaged in a session or particular type of session, the provider may not be assigned to the role. Further, a provider may not be allowed to be assigned to a particular role if they are currently assigned to a conflicting role. Alternatively, a provider might not be allowed to be assigned to a given role unless they are also assigned to a dependent role. Similar rules and criteria may be used to un-assign a provider from a role. Further, a provider may register for a role in any number of ways. Although an IVR example was provided in association with FIG. 3, a provider may be able to register via a web browser, a proprietary interface, or the like. In a preferred embodiment, the provider is able to use a web browser to access a web page, which facilitates registration in general and selection of roles and any associated scheduling.

Since the role server 20 may reside in the session control path, various options are available to provide information to the requester as well as receive information from the requester. For example, the role server 20, or other entity in the session control path, may provide call progress updates, provider status or availability, service information, or the like to the requester as the role server 20 is selecting a provider and establishing a media session with the provider. Such information may also be provided while the media session is in progress, on hold, or being transferred. The role server 20 may also allow the requester to provide supplemental information to the role server 20 as the role server 20 is selecting a provider and establishing a media session with the provider. Such information may also be provided while the media session is in progress, on hold, or being transferred. The supplemental information may be used as a factor in dynamically controlling assignment of the provider to various roles (assignment rules); selecting of a provider who is assigned to a role to respond to a session request (provider selection rules); or routing of a session request to one or more provider terminals 16 of a provider after the provider has been selected for the session request (provider routing rules). For example, a requester may be provided the opportunity to change the status associated with the initial session request while the requested media session is being established. The change in status may affect selection of a provider or provider terminal 16 for the session request. The information exchange may take place in the same or different media session.

Figure 7A:
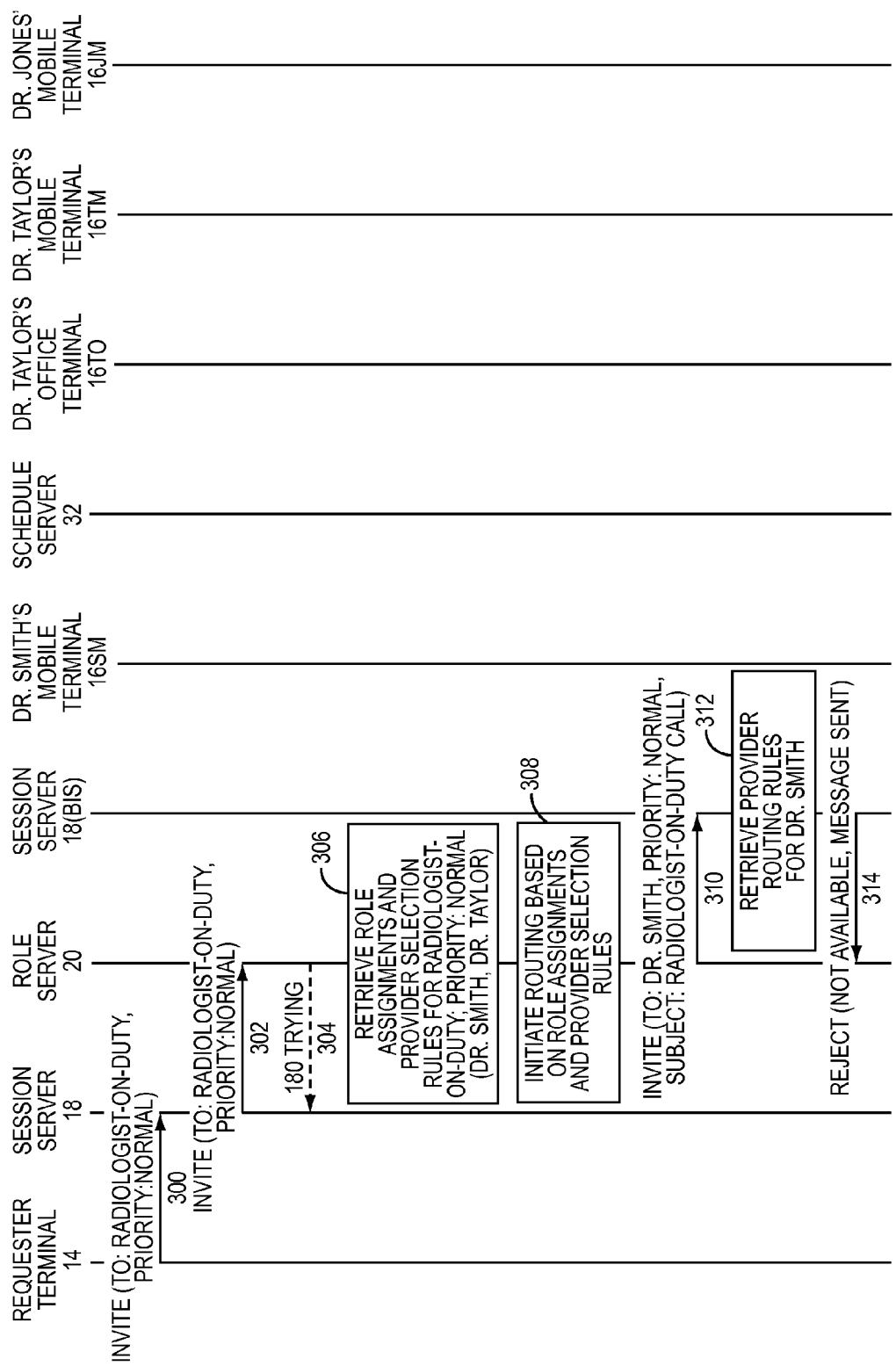
FIGS. 7A and 7E are a communication flow illustrating an exemplary registration, assignment, and routing process according to one embodiment of the present invention.
Figure 7B:
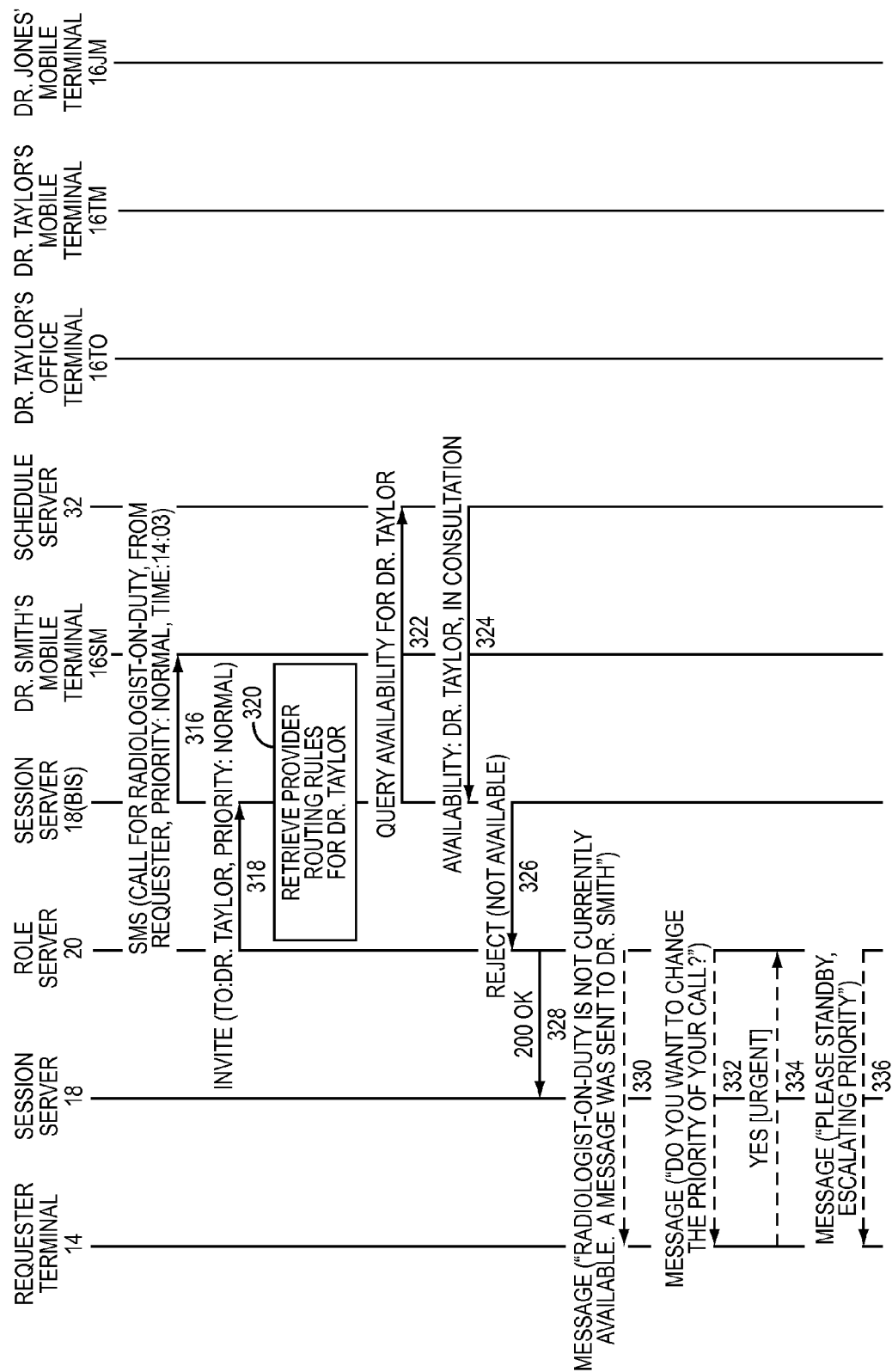
Figure 7C:
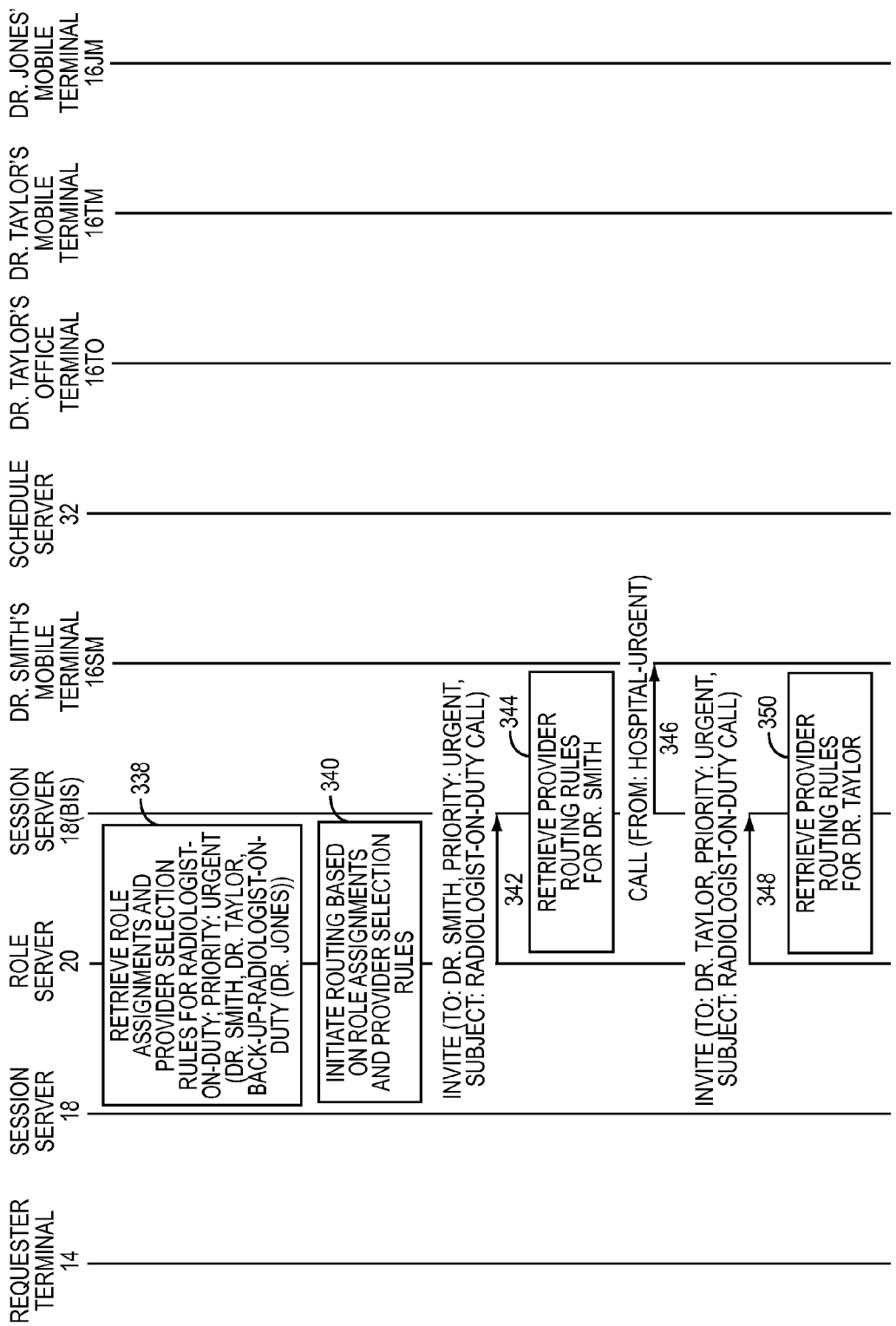
Figure 7D:
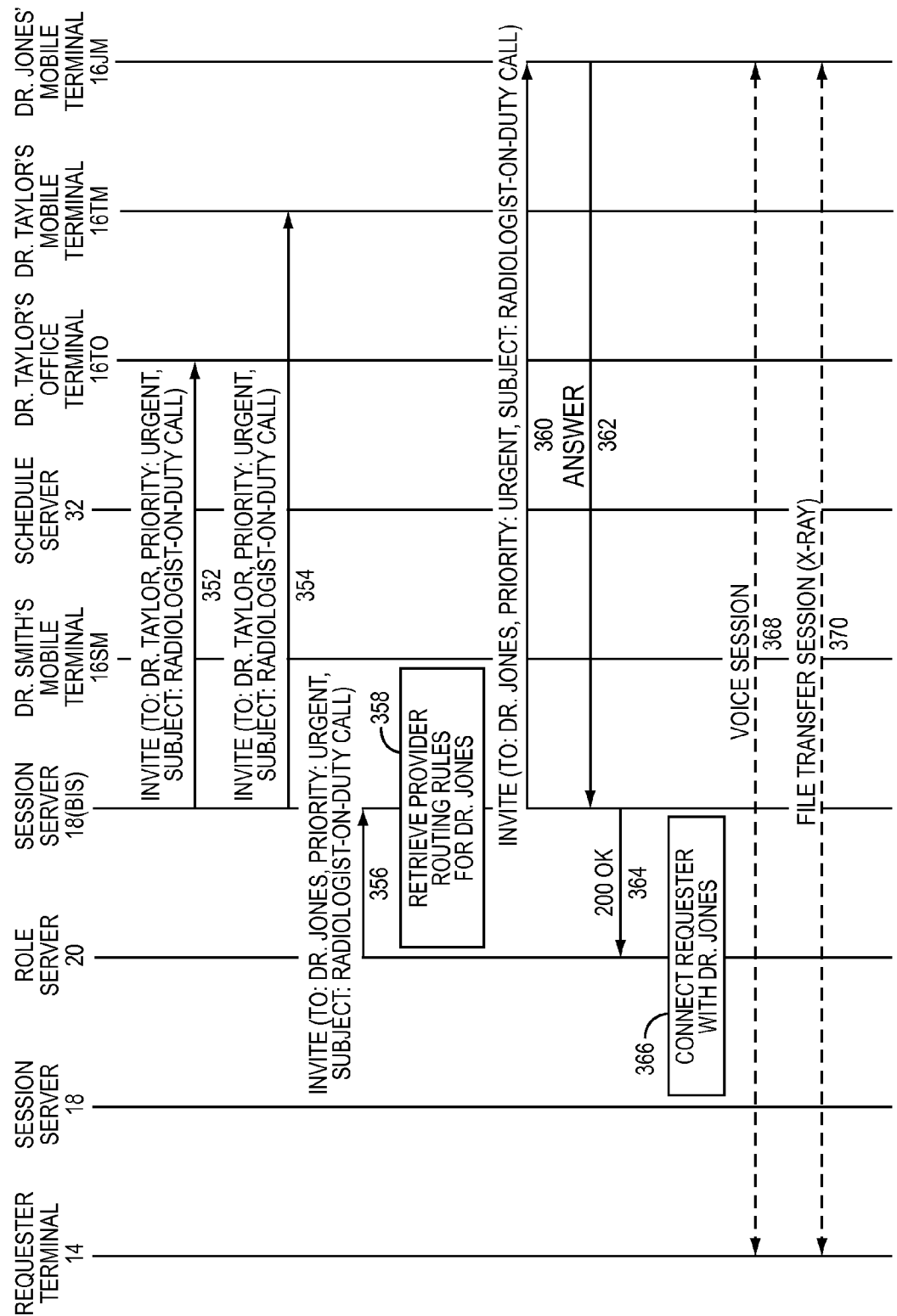
Figure 7E:
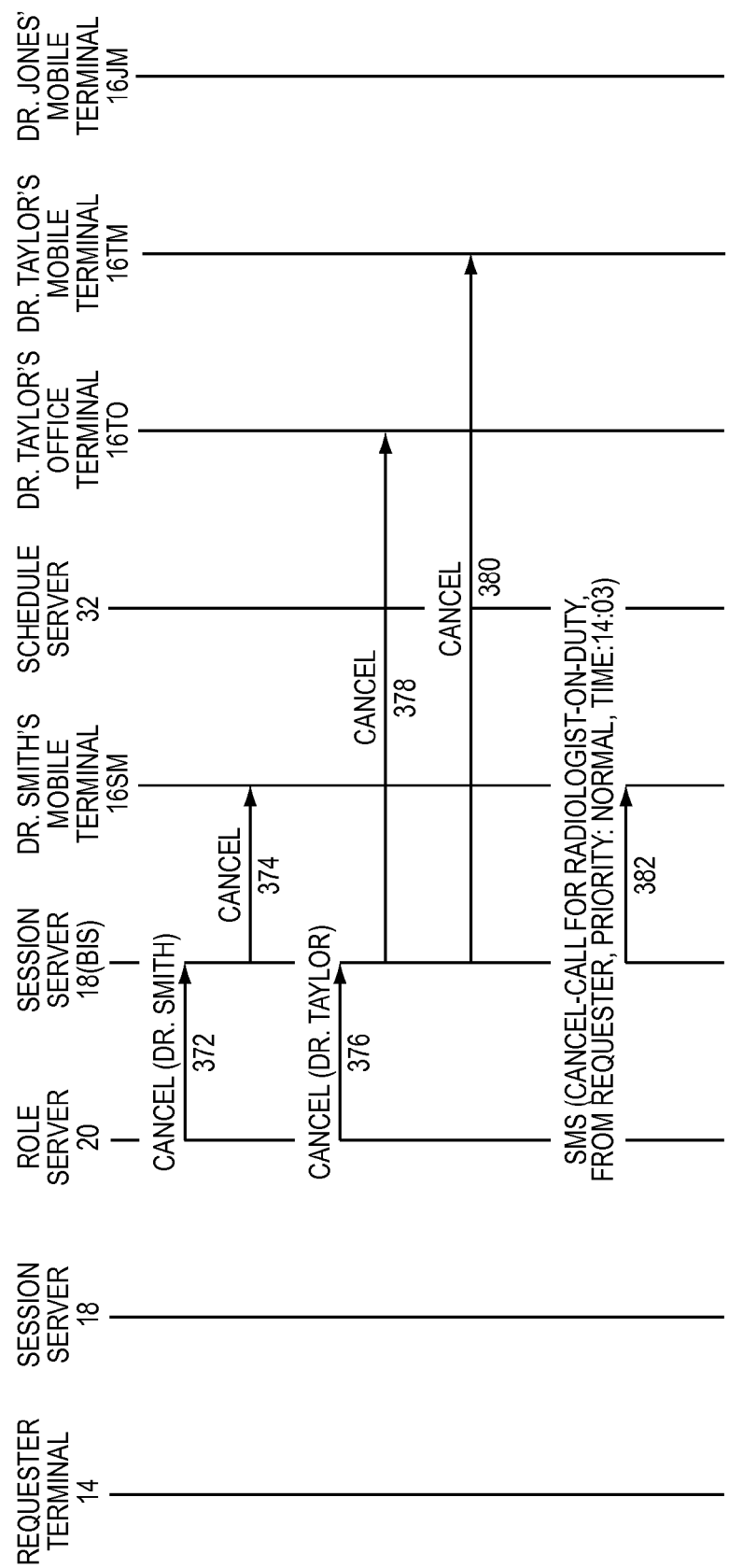

With reference to FIGS. 7A and 7E, a communication flow illustrates an exemplary session routing scenario according to one embodiment of the present invention. Again, it is assumed the session server 18 and the role server 20 operate in a set environment. Those skilled in the art will recognize the concepts illustrated herein may apply to any type of communication environment. Initially, assume a requester associated with the requester terminal 14 desires to talk to a radiologist, and as such, initiates a session directed to the role of "radiologist-on-duty," and not a particular radiologist. Accordingly, the requester will instruct the requester terminal 14 to initiate a call directed toward an address, directory number, or the like corresponding to the "radiologist-on-duty" role. As such, as shown in FIG. 7A, the requester terminal 14 may initiate an invite directed to the "radiologist-on-duty" role, uniform resource identifier (URI), or directory number. The session request in this example is for a voice session, or call. Further, assume that the initial session request is associated with a normal priority level. Although the invite is directed toward the "radiologist-on-duty" role, the invite may be sent directly or indirectly to a corresponding session server 18 (step 300). The session server 18 will determine the invite is intended for the "radiologist-on-duty" role and direct the invite to the role server 20, which acts as a proxy for the "radiologist-on-duty" role (step 302). At this point, the role server 20 will begin processing the invite, and in the meantime, will provide a 180 trying message back to the session server 18, to indicate that the session is being processed (step 304). Depending on the embodiment, the session server 18 may forward the 180 trying message to the requester terminal 14 or provide some other indication directly or indirectly to the requester terminal 14 to indicate that the session request is being processed.

Next, the role server 20 will retrieve the role assignments and provider selection rules for the "radiologist-on-duty" role when the session request is associated with a normal priority (step 306). Using the active role assignments as provided in the table of FIG. 5, Dr. Smith and Dr. Taylor are to be selected in a round robin fashion under the circumstances. The role server 20 will initiate routing based on the role assignments and the provider selection rules (step 308). Assume that Dr. Smith is initially selected to fulfill the request. The role server 20 will generate an invite intended for Dr. Smith, associated with a normal priority, and having a subject of "radiologist-on-duty call." The invite is sent toward a second instance of the session server 18 (BIS), which acts as a proxy for the provider terminal 16 of Dr. Smith (step 310). The session server 18 (BIS) may access any provider routing rules for Dr. Smith (step 312). The provider routing rules may dictate if, how, and when to route session requests to the particular provider terminal 16 of a given provider. In this example, assume the provider routing rules for Dr. Smith indicate that Dr. Smith is not available to respond to the request. Notably, the provider routing rules may have dynamically updated criteria, which is based on the presence, location, or schedule information of the provider. As such, Dr. Smith may be consulting another patient, and as such is not available to respond to the requester. The provider routing rules may also provide additional instructions for providing a message to Dr. Smith to indicate that an attempt was made to contact her. In this example, the session server 18 (BIS) will respond to the provider routing rules by sending a reject message back to the role server 20 in response to the invite (step 314). The reject message will indicate that Dr. Smith is not available and that a message will be sent to Dr. Smith to indicate that an attempt was made to have Dr. Smith respond to the request. Referring now to FIG. 7B, a short message service (SMS) message may be sent to Dr. Smith's mobile terminal 16SM to indicate that she missed a call from the requester at a particular time (step 316).

The role server 20 may respond to Dr. Smith rejecting the first routing attempt by selecting the next provider that is assigned to the "radiologist-on-duty" role. As such, Dr. Taylor is selected and a corresponding invite is sent toward Dr. Taylor (step 318). In particular, the invite may be sent to the second instance of the session server 18 (BIS) and the second instance of the session server 18 (BIS) may retrieve the provider routing rules for Dr. Taylor (step 320). Assume the provider routing rules for Dr. Taylor dictate that Dr. Taylor's schedule be accessed to determine his availability. As such, the session server 18 (BIS) will send a query to the schedule server 32 to determine Dr. Taylor's availability (step 322). The schedule server 32 will determine Dr. Taylor's availability, and in this instance, respond by indicating that Dr. Taylor is not available, because he is also in consultation with a patient (step 324). The session server 18 (BIS) will once again send a reject message back to the role server 20 to indicate that Dr. Taylor is not available (step 326). However, in this instance, Dr. Taylor does not have provider routing rules dictating that messages be sent to him to indicate that such attempts were made. The role server 20 will send a 200 OK message back to the session server 18 to establish a voice session between the requester terminal 14 and an IVR function 36, which is associated with the role server 20 (step 328). The role server 20 may be configured to send a message to the requester over the voice session to indicate that a "radiologist-on-duty is not available" and that "a message was sent to Dr. Smith" (step 330). The role server 20 may follow up with another message asking the requester "do you want to change the priority of your call?" (step 332). In this example, assume the requester responds by indicating that they do want to change the priority of the call to urgent by a voice or DTMF command, which is delivered to the role server 20 via the IVR function 36 (step 334). The role server 20 may respond by having the IVR function 36 tell the requester to "please stand by, escalating priority" (step 336).

At this point, now referring to FIG. 7C, the role server 20 will retrieve the role assignments and provider selection rules for the "radiologist-on-duty" role where the priority of the session request is urgent (step 338). In this example, the provider selection rules dictate that Dr. Smith, Dr. Taylor, and the provider fulfilling the "back-up-radiologist-on-duty" role be contacted either sequentially or simultaneously. In this case, the "back-up-radiologist-on-duty" role is being fulfilled by Dr. Jones. The role server 20 will initiate routing based on the role assignments and the provider selection rules (step 340). Initially, the role server 20 will send an invite to Dr. Smith wherein the invite indicates that the session request is urgent and that it relates to a request to talk to a "radiologist-on-duty." The invite is sent toward the second instance of the session server 18 (BIS) (step 342), which will respond by retrieving the provider routing rules for Dr. Smith (step 344). In this example, assume that the provider routing rules dictate that urgent calls be sent to Dr. Smith's mobile terminal 16SM, and as such, the session server 18 (BIS) will initiate a call toward Dr. Smith's mobile terminal 16SM, in a direct or indirect fashion (step 346).

While an attempt is being made to reach Dr. Smith, an attempt is also being made to reach both Dr. Taylor and Dr. Jones. For Dr. Taylor, the role server 20 will initiate an invite toward Dr. Taylor (step 348). Again, the session server 18 (BIS) will receive the invite and retrieve the provider routing rules for Dr. Taylor (step 350). For urgent calls directed to Dr. Taylor, the provider routing rules will dictate simultaneous calls to Dr. Taylor's office terminal 16TO as well as Dr. Taylor's mobile terminal 16TM. As such, now referring to FIG. 7D, invites are sent to Dr. Taylor's office terminal 16TO and Dr. Taylor's mobile terminal 16TM (steps 352 and 354).

For Dr. Jones, the role server 20 will send an invite to the second instance of the session server 18 (BIS) (step 356), and the session server 18 (BIS) will retrieve the provider routing rules for Dr. Jones (step 358). For an urgent request, the provider routing rules for Dr. Jones require an attempt to contact Dr. Jones on her mobile terminal 16JM. As such, an invite is sent to Dr. Jones' mobile terminal 16JM (step 360). The invite may indicate that the priority is urgent and include subject information, such that it is a call attempt for the "back-up-radiologist-on-duty" role.

Assume that Dr. Jones is the first of the three doctors, Dr. Smith, Dr. Taylor, and Dr. Jones, to respond. In particular, assume Dr. Jones responds by answering her mobile terminal 16JM, and as such, an answer message is delivered back to the second instance of the session server 18 (BIS) (step 362). The session server 18 (BIS) will attempt to establish a voice session with a requester terminal 14 by delivering a 200 OK message back toward the role server 20 (step 364). The role server 20 will effectively connect the voice session that was established earlier between the IVR function 36 and the requester terminal 14 with Dr. Jones' mobile terminal 16JM (step 366). Regardless of how the voice session is established, the voice session is directly or indirectly provided between the requester terminal 14 and the mobile terminal 16JM of Dr. Jones (step 368). In addition to the voice session, a file transfer session may be established between a requester terminal 14 of the requester and a provider terminal 16 of Dr. Jones. The requester terminal 14 for the file transfer session may be the same or a different requester terminal 14 that was used to establish the voice session. Similarly, the file transfer session may be established with any device of Dr. Jones, including the mobile terminal 16JM. In the file transfer session, the requester may provide various information, such as a digital representation of an x-ray, to Dr. Jones, and Dr. Jones may provide information to the requester, such as forms, prescriptions, and the like (step 370).

Notably, even though a voice session has been established between the requester and Dr. Jones, attempts to initiate the voice session with Dr. Smith and Dr. Taylor are still being made. Once Dr. Jones engages in the voice session, the role server 20 may take the necessary steps to cancel the attempts to initiate voice sessions with Dr. Smith's mobile terminal 16SM, Dr. Taylor's office terminal 16TO, and Dr. Taylor's mobile terminal 16TM. Referring now to FIG. 7E, for Dr. Smith's mobile terminal 16SM, the role server 20 will send a cancel message toward the session server 18 (BIS), which will forward the cancel message toward Dr. Smith's mobile terminal 16SM (steps 372 and 374). The role server 20 will also cancel the attempts being made to Dr. Taylor by sending a single cancel message toward the session server 18 (BIS) (step 376), which will send cancel messages toward both Dr. Taylor's office terminal 16TO and mobile terminal 16TM (steps 378 and 380).

As noted above, the provider routing rules for Dr. Smith require an SMS message be sent to Dr. Smith's mobile terminal 16SM when a call is missed or otherwise not responded to. As such, the second instance of the session server 18 (BIS) may provide an SMS message indicating that an attempt to contact Dr. Smith through her mobile terminal 16SM was cancelled and that the associated priority with the session request was urgent. The time of the initiate session request may also be included along with the identity of the requester (step 382).

Figure 8:
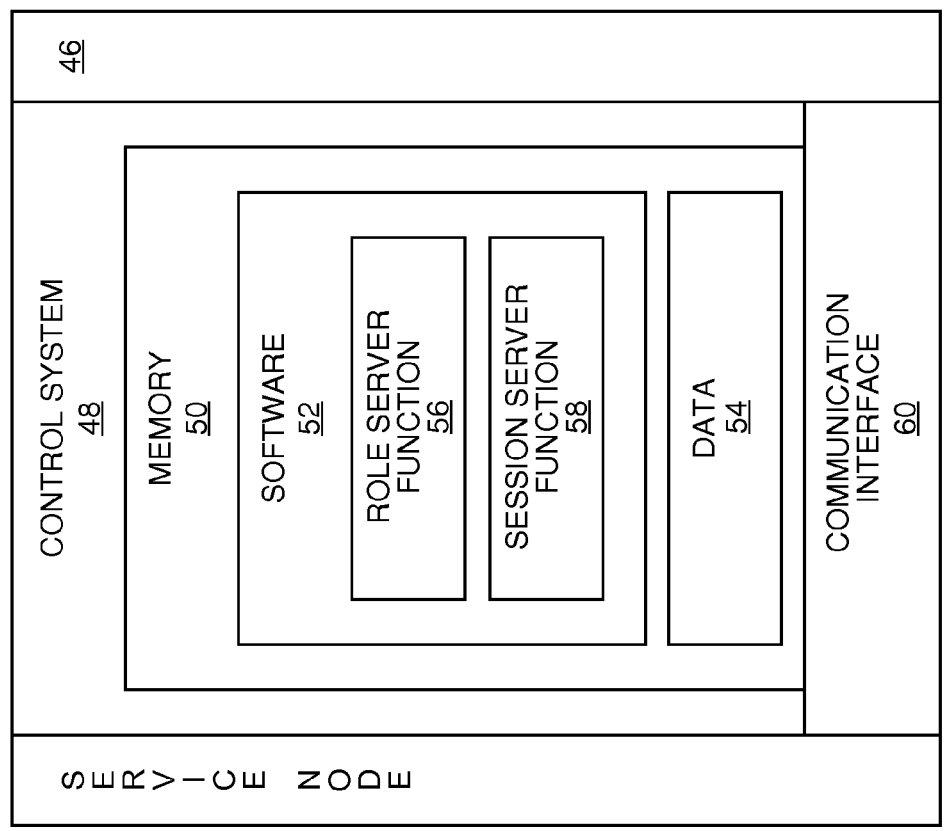
FIG. 8 is a block representation of a service node according to one embodiment of the present invention.

With reference to FIG. 8, a service node 46 is illustrated according to one embodiment of the present invention. The service node 46 may represent the role server 20, the session server 18, or a combination of the functionality therein. As such, the service node 46 may include a control system 48 having sufficient memory 50 for the requisite software 52 and data 54 to operate as described above. The software 52 may include one or both of a role server function 56 and a session server function 58. The role server function 56 provides the functionality of the role server 20 wherein the session server function 58 provides the functionality of the session server

18. The control system 48 may also be associated with a communication interface 60 to facilitate communications with various entities in the communication environment 10 over the communication network 12.

Those skilled in the art will recognize improvements and modifications to the preferred embodiments of the present invention. All such improvements and modifications are considered within the scope of the concepts disclosed herein and the claims that follow.

What is claimed is:

1. A method comprising:
    receiving a session request in response to a requester initiating a communication session toward a desired role;
    identifying a provider who is assigned to the desired role;
    assigning each of a plurality of providers to one or more of at least two roles wherein the provider is one of the plurality of providers and the desired role is one of the at least two roles;
    receiving information bearing on whether an assignment criterion has been met;
    determining whether the assignment criterion has been met, wherein the provider is automatically assigned to the desired role upon determining the assignment criterion has been met;
    automatically de-assigning the provider from the desired role after the provider is assigned to the desired role and upon determining the assignment criterion is not met;
    identifying at least one provider terminal associated with the provider; and
    routing the session request toward the at least one provider terminal.

2. The method of claim 1 wherein the provider is concurrently assigned to at least two different roles of the at least two roles and the desired role is one of the at least two different roles.

3. The method of claim 1 further comprising:
    receiving from the provider a registration request that identifies the desired role to which the provider desires to be assigned; and
    determining whether to register the provider for the desired role in response to the registration request, wherein the provider is assigned to the desired role after being registered.

4. The method of claim 1 wherein the assignment criterion is presence information of the provider and the provider is assigned to the desired role and de-assigned from the desired role when the presence information changes.

5. The method of claim 1 wherein the assignment criterion is a location of the provider and the provider is assigned to the desired role and de-assigned from the desired role when the location changes.

6. The method of claim 1 wherein the assignment criterion is schedule information of the provider and the provider is assigned to the desired role and de-assigned from the desired role when the schedule information changes.

7. The method of claim 1 wherein at least two providers, including the provider, are assigned to the desired role and identifying the provider who is assigned to the desired role comprises:
    identifying the desired role from the session request; and
    selecting the provider from the at least two providers based on a role selection criterion.

8. The method of claim 7 wherein the role selection criterion is presence information of the provider and the provider is selected based on the presence information.

9. The method of claim 7 wherein the role selection criterion is a location of the provider and the provider is selected based on the location.

10. The method of claim 7 wherein the role selection criterion is schedule information of the provider and the provider is selected based on the schedule information.

11. The method of claim 7 wherein the role selection criterion is a relative priority identified in the session request and the provider is selected based on the relative priority.

12. The method of claim 1 wherein at least two provider terminals, including the at least one provider terminal, are associated with the provider and identifying the at least one provider terminal associated with the provider comprises selecting the at least one provider terminal from the at least two provider terminals based on a routing selection criterion.

13. The method of claim 12 wherein the routing selection criterion is presence information of the provider and the at least one provider terminal is selected based on the presence information.

14. The method of claim 12 wherein the routing selection criterion is a location of the provider and the at least one provider terminal is selected for the desired role based on the location.

15. The method of claim 12 wherein the routing selection criterion is schedule information of the provider and the at least one provider terminal is selected for the desired role based on the schedule information.

16. The method of claim 12 wherein a plurality of the at least two provider terminals are selected and the session request is routed toward each of the at least two provider terminals.

17. The method of claim 12 wherein the routing selection criterion is a relative priority identified in the session request and the at least one provider terminal is selected based on the relative priority.

18. The method of claim 1 wherein identifying the provider who is assigned to the desired role comprises selecting a plurality of providers who are assigned to the desired role and routing the session request toward the at least one provider terminal comprises routing the session request toward a plurality of provider terminals, each of which being associated with a unique one of the plurality of providers.

19. The method of claim 1 further comprising effecting delivery of session progress information to the requester to provide information bearing on how establishment of the communication session is progressing.

20. The methods of claim 1 further comprising effecting delivery of availability information to the requester to provide information bearing on an availability of the provider for the communication session.

21. The method of claim 1 further comprising:
    receiving additional information from the requester after the session request is routed to the at least one provider terminal;
    identifying a second provider who is assigned to the desired role;
    identifying a provider terminal associated with the second provider; and
    routing the session request toward the provider terminal.

22. The method of claim 1 wherein the session request is associated with a first priority and the session request is routed to the at least one provider terminal identifying the first priority, the method further comprising:
    prior to establishing the communication session with the provider, receiving from the requester additional information indicative of the first priority being changed to a second priority; and delivering information to the provider indicative of the session request being associated with the second priority.

23. The method of claim 1 wherein the communication session is established in part using a session initiation protocol.

24. The method of claim 1 wherein the communication session is a voice session.

25. The method of claim 1 wherein the session request is ultimately routed to a voicemail box assigned to the desired role.

26. The method of claim 1 wherein the session request is ultimately routed to a back-up role if the provider is not available for the communication session.

27. The method of claim 1 wherein the session request is routed to a queue until the provider is available for the communication session.

28. A system comprising:
   at least one communication interface; and
   a control system associated with the at least one communication interface and configured to:
      receive a session request in response to a requester initiating a communication session toward a desired role;
      identify a provider who is assigned to the desired role;
      assign each of a plurality of providers to one or more of at least two roles wherein the provider is one of the plurality of providers and the desired role is one of the at least two roles;
      receive information bearing on whether an assignment criterion has been met;
      determine whether the assignment criterion has been met, wherein the provider is automatically assigned to the desired role upon determining the assignment criterion has been met;
      automatically de-assign the provider from the desired role after the provider is assigned to the desired role and upon determining the assignment criterion is not met;
      identify at least one provider terminal associated with the provider; and
      route the session request toward the at least one provider terminal.

29. The system of claim 28 wherein the control system is further configured to assign each of a plurality of providers to one or more of at least two roles wherein the provider is one of the plurality of providers and the desired role is one of the at least two roles.

30. The system of claim 28 wherein at least two providers, including the provider, are assigned to the desired role, and to identify the provider who is assigned to the desired role, the control system is further configured to:
   identify the desired role from the session request; and
   select the provider from the at least two providers based on a role selection criterion.

* * * * *